US011402485B2

(12) United States Patent
Jain et al.

(10) Patent No.: US 11,402,485 B2
(45) Date of Patent: Aug. 2, 2022

(54) ULTRA-WIDEBAND INTELLIGENT SENSING SYSTEM AND METHOD

(71) Applicant: Robert Bosch GmbH, Stuttgart (DE)

(72) Inventors: Vivek Jain, Sunnyvale, CA (US); Sushanta Mohan Rakshit, Santa Clara, CA (US); Yunze Zeng, San Jose, CA (US)

(73) Assignee: Robert Bosch GmbH, Stuttgart (DE)

( * ) Notice: Subject to any disclaimer, the term of this patent is extended or adjusted under 35 U.S.C. 154(b) by 463 days.

(21) Appl. No.: 16/398,571

(22) Filed: Apr. 30, 2019

(65) Prior Publication Data

US 2020/0348406 A1 Nov. 5, 2020

(51) Int. Cl.
| | | |
|---|---|---|
| *G01S 13/56* | (2006.01) | |
| *G01S 13/02* | (2006.01) | |
| *G01S 13/18* | (2006.01) | |
| *G06F 17/14* | (2006.01) | |
| *G05D 1/02* | (2020.01) | |
| *A61B 5/18* | (2006.01) | |

(Continued)

(52) U.S. Cl.
CPC .............. *G01S 13/56* (2013.01); *A61B 5/024* (2013.01); *A61B 5/113* (2013.01); *A61B 5/18* (2013.01); *G01S 13/0209* (2013.01); *G01S 13/18* (2013.01); *G05D 1/028* (2013.01); *G05D 1/0231* (2013.01); *G06F 17/142* (2013.01)

(58) Field of Classification Search
CPC ........... A61B 5/024; A61B 5/113; A61B 5/18; G01S 13/0209; G01S 13/04; G01S 13/18; G01S 13/56; G01S 13/878; G01S 13/886; G01S 7/415; G01S 7/417; G05D 1/0231; G05D 1/028; G06F 17/142; G07C 2009/00793; G07C 9/00309
See application file for complete search history.

(56) References Cited

U.S. PATENT DOCUMENTS

| | | |
|---|---|---|
| 7,196,629 B2 | 3/2007 | Ruoss et al. |
| 8,335,599 B2 | 12/2012 | Dickerhoof et al. |
| 9,553,694 B1 | 1/2017 | Elangovan et al. |

(Continued)

OTHER PUBLICATIONS

Sharma et al.; Device-Free Activity Recognition Using Ultra-Wideband Radios; pp. 1029-1033; 2019 IEEE; International Conference on Computing, Networking and Communications (ICNC).

(Continued)

*Primary Examiner* — Timothy X Pham
(74) *Attorney, Agent, or Firm* — Brooks Kushman P.C.

(57) ABSTRACT

A system and method is disclosed where an operating state may be determined by selecting one or more transmitting nodes for transmitting one or more radio-frequency (RF) signals. One or more receiving nodes may receive the one or more RF signals that may include one or more channel state data. The operating state may be determined based on one or more features extracted from the one or more channel state data. Another system and method is disclosed where a range compensation value may be determined by transmitting a radio-frequency (RF) signal from at least one transmitting node. The one or more receiving nodes may receive the RF signal and a channel state data may be estimated using the signal. The range compensation value may be determined using the channel state data and a position value indicating a location of the at least one transmitting node.

19 Claims, 10 Drawing Sheets

(51) Int. Cl.
  *A61B 5/113*    (2006.01)
  *A61B 5/024*    (2006.01)

(56) References Cited

U.S. PATENT DOCUMENTS

| | | |
|---|---|---|
| 10,156,852 B2 | 12/2018 | Bakhishev et al. |
| 2014/0093021 A1* | 4/2014 | Jain ................... H04L 25/023 |
| | | 375/346 |
| 2018/0234797 A1 | 8/2018 | Ledvina et al. |
| 2018/0365975 A1* | 12/2018 | Xu ........................ G01V 3/12 |
| 2019/0004155 A1* | 1/2019 | Eber ................... G01S 7/4865 |
| 2019/0007256 A1* | 1/2019 | Chen ................... H04L 5/0048 |
| 2021/0190940 A1* | 6/2021 | Troutman ............ G01S 13/878 |

OTHER PUBLICATIONS

Hillyard et al.; Experience: Cross-Technology Radio Respiratory Monitoring Performance Study; MobiCom '18, Oct. 29-Nov. 2, 2018, New Delhi, India; pp. 487-496.

* cited by examiner

ULTRA-WIDEBAND INTELLIGENT SENSING SYSTEM AND METHOD

TECHNICAL FIELD

The following relates generally to an ultra-wideband sensing system and method that may provide increased context awareness, safety, and security.

BACKGROUND

For automotive applications, keyless entry systems provide remote access allowing users the ability to remotely lock or unlock vehicle doors. For instance, key fobs include buttons for locking/unlocking vehicle doors. More recently, automotive manufacturers have begun to introduce what is referred to as passive keyless system. Passive keyless systems may not require pressing a button to lock/unlock vehicle doors. Passive keyless systems also may not require a physical key to start the vehicle. Instead, passive keyless systems may allow such actions to be performed when the key fob is located near or within the vehicle.

SUMMARY

A system and method is disclosed where an operating state may be determined by selecting one or more transmitting nodes for transmitting one or more radio-frequency (RF) signals. One or more RF signals may then be received at one or more receiving nodes. The one or more RF signals may include one or more channel state data. The receiving nodes may estimate channel state date from one or more received signals as well. The operating state may then be determined based on one or more features extracted from the one or more channel state data.

The channel state data may be channel impulse response (CIR) metadata associated with an ultra-wide band (UWB) signal. The system and method may then be operable to determine the operating state by computing a difference between a first path of a CIR metadata and a peak path position of the CIR metadata. It is contemplated that the difference between the first path and peak path may be greater for a non-line of sight operating state than for a line of sight operating state.

The channel state data may be channel impulse response (CIR) data associated with an ultra-wide band (UWB) signal. It is also contemplated that the channel state data may include at least one of a peak position, amplitude, or phase. The system and method may then be operable to determine the operating state by estimating and correlating CIR data under various vehicle states and environmental states. The correlations may be higher for a given state matching a pre-determined operating state. The system and method may also determine sudden user activity within a vehicle by detecting large changes in the one or more CIRs. The system and method may also detect a difference between an inanimate object and a user, or between an adult and a child.

The system and method may further differentiate between a first user and a second user based on reflection patterns detected within the one or more channel state data. Lastly, the system and method may activate an intrusion system (e.g., an audible alarm) when it is determined that a vehicle is unoccupied and the vehicle doors are shut and locked and a user is detected as being near the unoccupied and locked vehicle. The system and method may further utilize channel state data to adjust estimated range between two communicating devices. The range compensation value may be adjusted based on a known or estimated position value or location zone value of the at least one transmitting node or a sensed environmental condition.

For example, the sensed environmental conditions could include a vehicle being parked next to a second vehicle, the vehicle being parked next to a wall, a human being in the vicinity of the vehicle, inanimate objects being detected within the vehicle, humans being detected within the vehicle, or the vehicle being located near any other external object. It is also contemplated that the range compensation value may be adjusted using a statistical range correction factor encompassing all possible scenarios for a give node or for all nodes on the vehicle. It is also contemplated that the range compensation value may be estimated using sensed environmental conditions. It is further contemplated that the range compensation value may be adjusted based on a correlation of the channel state data with training data obtained during a machine-learning training process.

In another embodiment, a node located within a vehicle may transmit an ultra-wide band (UWB) signal to a target device within communication range. A response message including CIR data calculated from the UWB signal may then be transmitted from the target device to the node. The response message may be processed by the node to determine a correlation between the CIR calculated form received UWB signal and the CIR data included within the response message. A correlation may exist if both the node and target device estimate similar CIRs establishing authenticity of the communication link.

It is also contemplated that the target device located remote of the vehicle may transmit an ultra-wide band (UWB) signal to the node located within the vehicle. A response message including CIR data calculated from the UWB signal may then be transmitted from the node to the target device. The response message may be processed by the target device to determine a correlation between the CIR calculated from received UWB signal and the CIR data included within the response message. Again, a correlation may exist if both the target device and the node estimate similar CIRs establishing authenticity of the communication link.

The system and method may further include processing the one or more channel state data using a Fast Fourier Transformation (FFT) algorithm and a Discrete Wavelet Transform (DFT) algorithm. The channel state data may also be filtered using one or more bandpass filtering algorithms to allow detection of a user heart rate, detection of a user breathing rate, differentiating between an inanimate object and a user, or differentiating between an adult and a child Also, the channel state data may be processed using a machine-learning classification algorithm (e.g., a Random Forest classification algorithm).

DETAILED DESCRIPTION

Figure 1:
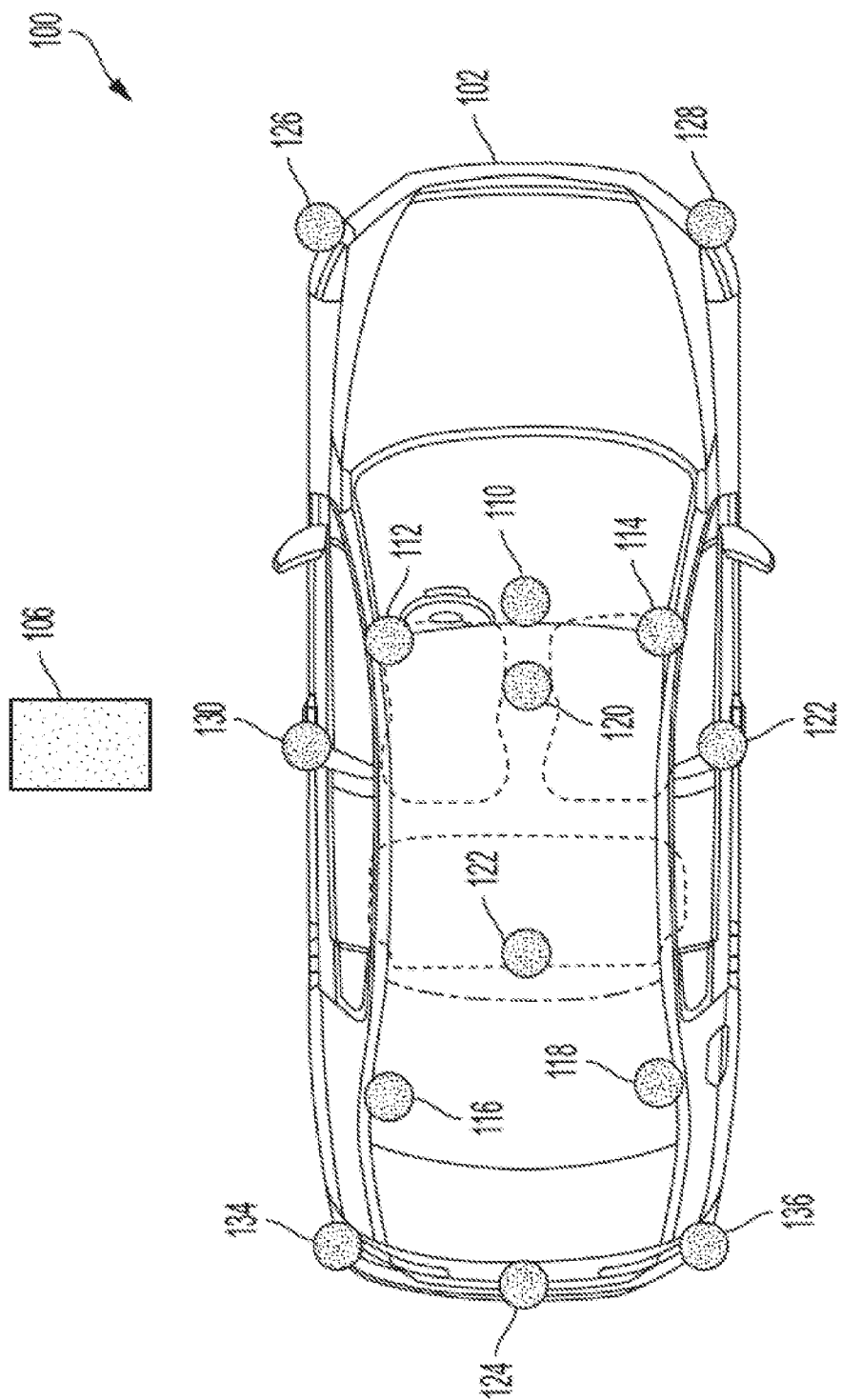
FIG. 1 is an illustrative example of the ultra-wide band sensing (UWB) system located within a vehicle.

As required, detailed embodiments are disclosed herein; however, it is to be understood that the disclosed embodiments are merely exemplary and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present embodiments.

With the ongoing advancements in wireless technologies, people now use any number of connected and personalized services. As the number of wireless systems and services increases, manufacturers have begun to leverage such pre-existing systems and services in a different way than what was originally contemplated. For instance, manufacturers have begun to leverage radio frequency (RF) transceivers (such as WiFi) to track moving humans through walls and behind closed doors. The use of WiFi to track human movement is much different than the original use-case of a way to communicate data between electronic devices. By leveraging a pre-existing system beyond an intended application, manufacturers have been able to reduce the need for extra hardware which in turn reduces cost, space and/or provide increased power savings.

In automotive applications, key fobs have become more common for certain functions. For instance, when a user is located within the vicinity of a vehicle, the key fob may be used to automatically unlock doors. Or when a user is located within the vehicle, the key fob may allow the user to start the vehicle using a push button. To perform these functions, a key fob will wirelessly communicate and perform an authentication process. Currently, automotive manufacturers may rely on two types of radio frequency (RF) technologies. For passive entry systems (PES) and comfort entry go (CEG) applications, a low frequency (LF) technology may be used for key fob proximity and localization. For remote keyless entry, ultra-high frequency (UHF) technology may be employed. However, traditional LF and UHF technologies may not be adequate for additional leveraging. For instance, traditional LF and UHF technologies may not be capable of performing detection of users within a vehicle. As a result, additional systems may be required to perform such functionality. Also, LF and UHF systems have been known to be subjected to security breaches including "relay" attacks. There exists a need to provide a single system that can operate to provide more than just vehicle access and starting capabilities and to provide a system that can perform such functionality with improved security.

As disclosed by U.S. patent application Ser. No. 16/042, 397, which is incorporated herein by reference, an Ultra-Wideband (UWB) system is disclosed and operable to perform certain automotive functions such as vehicular access (i.e., keyless entry). UWB technology may be preferred over LF and UHF technology because it may provide more robust functionality and improved security capabilities. It is contemplated that a UWB system may also be capable of providing increased context awareness, safety, and security applications.

FIG. 1 illustrates a system 100 that may include nodes 110-136 located at various locations around a vehicle 102. The number and location of nodes 110-136 may depend on the desired accuracy, application, performance, and/or the make and model of the vehicle 102. For instance, the system 100 may include one or more nodes 112 that are able to monitor a sensing zone within and around the vehicle 102. Placement may allow the system 100 to use information received by nodes 110-124 to perform features internal to the vehicle 102 and nodes 126-136 to perform features external to the vehicle 102. For instance, based on information received from nodes 126-136 the system 100 may detect a user is within the vicinity of vehicle 102 and subsequently unlock the doors of vehicle 102. If there exists a stored user profile, system 100 may be operable to automatically adjust the vehicle seats, adjust the rear-view mirrors, activate the rear-view camera, adjust the HVAC system to a desired vehicle cabin temperature, or activate the in-cabin infotainment system.

Similarly, nodes 110-124 (i.e., internal nodes) may be used to start the vehicle 102 when the system 100 determines target device 106 is within the vehicle 102. system 100 may also be operable to perform the following functions: (1) detecting the state of the vehicle 102 (e.g., whether the vehicle 102 is unoccupied or occupied; or whether a door, window, or trunk is open); (2) monitoring the vital signs of an occupant within the vehicle 102 (e.g., heart rate, breathing rate, or user emotional state); (3) determining the occupancy of the vehicle 102 (i.e., count the number of living beings, humans and animals, within the vehicle 102); (4) detecting human movement or activity near the vehicle; (5) detecting the occupancy when a driver/passenger approaches (or leaves) the vehicle 102; and (6) detecting an intrusion in the vehicle 102 while ensuring complete privacy.

It is contemplated that one or more of these features may become desirable as autonomous (driverless) vehicles become more prevalent and a user's sense of security and well-being become more significant. With respect to security, it is contemplated that system 100 may be more robust to "relay" attacks because of the timing information that is employed using IEEE standard 802.15.4-2015. By employing a UWB standard like IEEE 802.15.4-2015, it is contemplated that messages may be sent and received by nodes 110-136 allowing the system 100 to infer a valid user is not located within the vicinity of the vehicle thwarting a relay attack.

Each node 110-136 may include a processor, memory, and a transceiver unit. The memory may be configured to store program instructions that, when executed by the processor, enable the nodes 110-136 to perform various operations described elsewhere herein, including localization of a target device 106 (e.g., a key fob, smart phone, or smart watch). The memory may be of any type of device capable of storing information accessible by the processor, such as write-capable memories, read-only memories, or other computer-readable mediums. Additionally, it will be recognized by those of ordinary skill in the art that a "processor" may include hardware systems, hardware mechanisms or hardware components that processes data, signals or other information. The processor may include a system with a central processing unit, multiple processing units, dedicated circuitry for achieving functionality, or other systems.

The nodes 110-136 may use an ultra-wideband transceiver configured to communicate with the target device 106. But nodes 110-136 may also include transceivers configured for communication with other electronic devices, including the ability to send communication signals and receive communication signals. The transceiver included within nodes 110-136 may comprise multiple ultra-wideband transceivers and/or multiple ultra-wideband antennas arranged in an array. The nodes 110-136 may also allow wireless or wired communication between the nodes 110-136 and/or communication with one or more control modules located within vehicle (e.g., ECU, HVAC system, security system) or external to the vehicle 102. The control module may also include a processor and memory that is operable to receive, store, and transmit information between the control module and the nodes 110-136. The control module may also be operable to control various systems (e.g., HVAC system) within the vehicle 102 based on the information received from the nodes 110-136.

Figure 2:
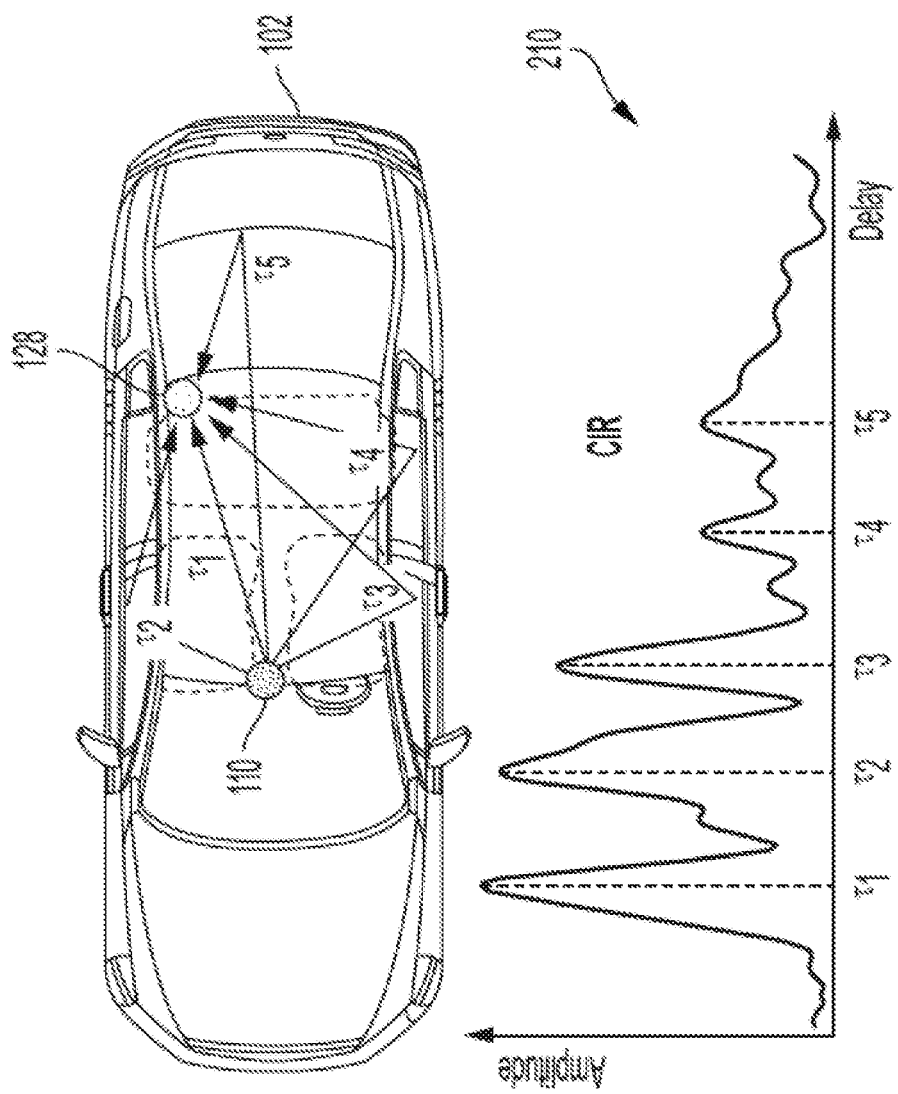
FIG. 2 is an illustrative example of the channel impulse response (CIR) signals seen by the UWB system.

Nodes 110-136 may be operable as a transceiver for sending and receiving a UWB message. One or more of nodes 110-136 may periodically transmit (or blink) a UWB message. One or more nodes 110-136 may perform the UWB-based sensing of car states using the channel impulse response (CIR) computed by a given receiver. For instance, FIG. 2 illustrates node 110 transmitting a UWB message that may be received by node 118. As illustrated, UWB message may be reflected at various points (shown by $\tau_1$-$\tau_5$) around the vehicle 102.

Graph 210 illustrates the CIR that may be computed by node 118 based on the reflected UWB message. As shown, the CIR for $\tau 1$ may have the greatest amplitude and the least amount of time delay because it was not reflected at any point within vehicle 102. Conversely, the CIR for $\tau 5$ may have one of the smallest amplitudes and the largest delays because it was reflected by a rear point (e.g., the trunk) of the vehicle 102 before being received by node 118.

Figure 3:
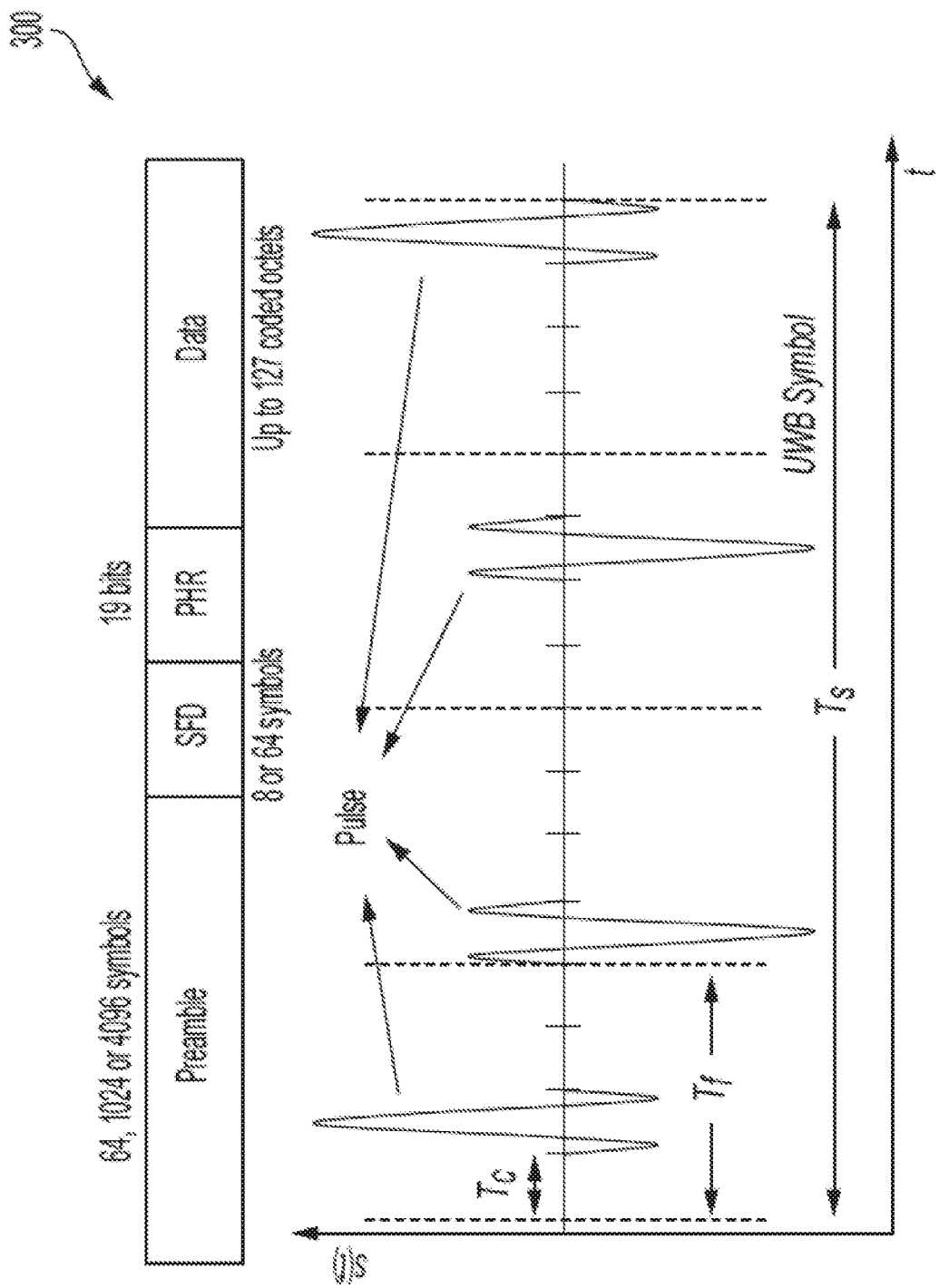
FIG. 3 is an illustrative example of a UWB signal.

FIG. 3 illustrates an exemplary UWB packet (message) that may be transmitted by nodes 110-136. The preamble of UWB packet may include a synchronization header that may be of a 64, 1024 or 4096 symbol-length known preamble sequence followed by an 8 or 64 symbol-length start of frame delimiter (SFD). A 19-bit physical header (PHR) may follow the SFD and include information for successful packet decoding such as the length and the data rate of the following data payload. The UWB symbol ($T_s$) may be comprised of multiple narrow pulses, and the pulses generated by the preamble may be used to compute the CIR when received by nodes 110-136. The exemplary UWB symbol shown includes a chipping sequence {1, 0, 2, 3} and the four exemplary pulses illustrate a polarity of +1, −1, −1, and +1. Each transmitted UWB symbol may be represented by Equation 1:

$$s(t)=\sqrt{E_p}*\Sigma_{j=0}^{N_f-1}b_j\omega(t-jT_f-c_jT_c) \quad (1)$$

Where $\omega(t)$ denotes the UWB pulse of duration Tp; $T_f$ may be the duration of a given frame (i.e., a symbol that may be divided into $N_f$ frames); $b_j \in \{-1, +1\}$ denotes the polarity code; $c_j$ denotes the hopping sequence; $T_c$ is the chip duration; and, $E_p$ represents the energy of the symbol. The hopping sequence $c_j$ may also be part of a set $\{1, 2 \ldots N_h\}$ where $N_h$ is the number of hopping slots (i.e., the hopping code may determine the location of the pulse within the $N_h$ slots of the frame).

As described with respect to FIG. 2, the UWB messages may travel wirelessly across multiple paths before being received by a given node. The signal received at a given node (e.g., node 122) for a given UWB message that is reflected by any number of different paths may be represented by Equation 2:

$$s(t)=\sqrt{E_p}*\Sigma_{j=0}^{N_f-1}\Sigma_{l=1}^{L}\alpha_l b_j\omega(t-\tau_l jT_f-c_jT_c) \quad (2)$$

Where $\alpha_l$ and $\tau_l$ refer to the complex attenuation and time of flight of the $l^{th}$ path. A UWB receiver included within nodes 110-136 may leverage the periodic auto-correlation property of the known preamble sequence illustrated by FIG. 3 to compute the CIR. In other words, the UWB receiver may correlate the received signal with the known preamble sequence to compute a channel impulse (CIR) which is represented by the following Equation 3:

$$h(t)=\Sigma_{l=1}^{L}\alpha_k\delta(t-\tau_l) \quad (3)$$

Where $\delta(.)$ represents the Dirac delta function. Nodes 110-136 may use this computed CIR to identify a car state by leveraging the intuition that the different states of the car may affect the CIR differently.

Figure 4:
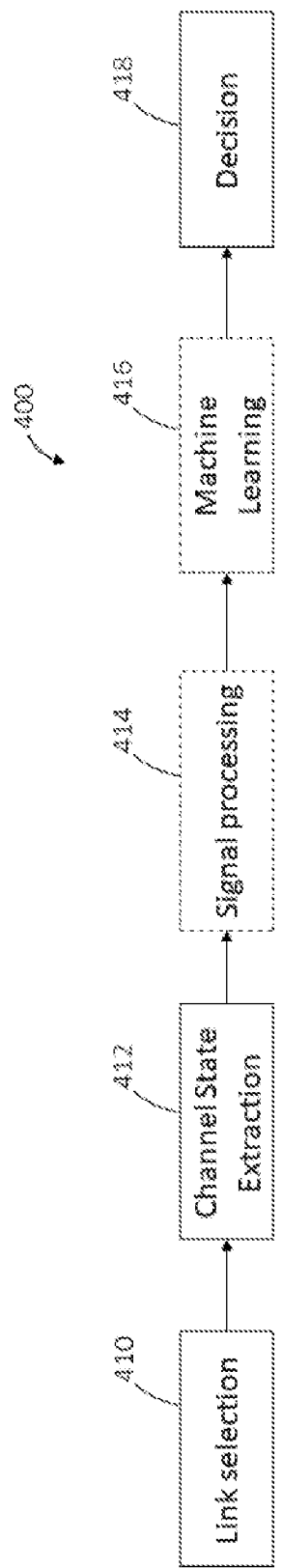
FIG. 4 is an illustrative operational diagram of the UWB system.

FIG. 4 illustrates a flow diagram 400 for how the system 100 may operate. At step 410, system 100 may select one of nodes 110-136 to operate as a transmitter. The link selection (i.e., node selection) of step 410 may be predetermined based on the calibration process performed by flow diagram 400. It is also contemplated that the transmitting node may be selected based on connectivity (UWB packet deliver rate) and the strength of the received packet and location of the nodes 110-136. In other words, the system 100 may determine which of the nodes 110-136 are operable to communicate with each other.

At step 412, the system 100 may operate on a given RF modality which may then be used by system 100 to determine a given operating state. For instance, system 100 may operate on a given RF signal property (i.e., channel information during communication) like CIR metadata to determine a given operating state. The CIR metadata may provide diagnostic information that system 100 may use to determine whether a received RF signal received is operating under a line-of-sight (LOS) or non-line-of-sight (NLOS) operating state. It is contemplated that the RF signal used for determining LOS or NLOS operating states may include UWB wireless technology (e.g., IEEE 802.15.4a), WiFi (e.g., 802.11), Bluetooth wireless technology (e.g., 802.15.1), or any other comparable RF technology.

System 100 may determine LOS and NLOS operating states by computing the difference between a first path of the CIR metadata and a peak path position of the CIR metadata. It is contemplated that the difference between the first path and peak path may be greater for NLOS conditions than for LOS operating states. System 100 may also evaluate the confidence level of the CIR metadata to determine whether a LOS or NLOS operating states exists. It is also contemplated that system 100 may use CIR metadata to evaluate a likelihood of undetected early paths to determine whether a LOS or NLOS condition exists.

It is contemplated that system 100 may determine NLOS or LOS operating states using any one of the CIR metadata (i.e., first path and peak path index, probability of NLOS estimate, confidence level, or likelihood of undetected early paths) alone. It is also contemplated that system 100 may combine one or more of the CIR metadata to more accurately determine whether a LOS or NLOS operating states exists.

The system 100 may also be programmed to detect or infer various operating states using nodes 110-136 alone, or in combination with other sensing systems (e.g., camera systems, ultrasonic systems, radar systems). For instance, system 100 may be operable to perform adaptive estimated range compensation based on the environment surrounding the vehicle 102. In traditional keyless systems, LF and UHF signals may be used to localize (i.e., estimate position) of a target access device (key fob, or phone). Localization using known keyless systems may require distance estimation of the target device with respective LF/UHF nodes located within the vehicle.

At step 414, the system 100 may apply signal processing algorithms to increase the resolution of each RF signal received. It is contemplated that step 414 may be optional and given applications may not require signal processing algorithms. For instance, system 100 may increase the resolution of a computed CIR by interpolating and upsampling in the frequency domain to aid in accurate alignment and feature extraction. If node 110 transmits a blink, nodes 112-136 may operate as anchors to receive and calculate the associated CIR. For a sampling frequency of 1 GHz, each CIR tap may be 1 nanosecond apart. The resolution of the CIR may be increased by an upsampling process where the system 100 can make the received response emulate the original analog waveform. By performing an upsampling process the system 100 may be able to more accurately align each CIR received by a given node.

At step 416, the system 100 may apply a machine-learning algorithm to assist in determining an operating state. It is contemplated that the machine-learning algorithm may employ known machine-learning classification algorithms like linear classifiers, support vector machines, decision trees, boosted trees, random forest, neural networks, or nearest neighbor.

At step 418, system 100 may determine a given operating state. Again, it is contemplated that system 100 may determine a given operating state based solely on the channel state extraction data received in step 412. Or at step 414 and step 416, the system 100 may determine a given operating state by further applying signal processing or a machine-learning algorithm.

Figure 5C:
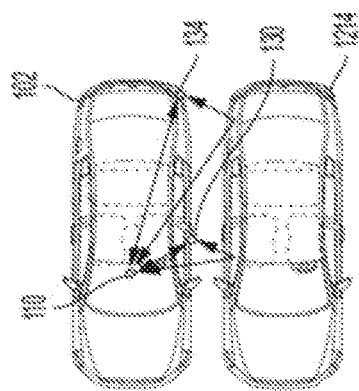
FIGS. 5A-5C are illustrative examples of the UWB system operation.
Figure 5B:
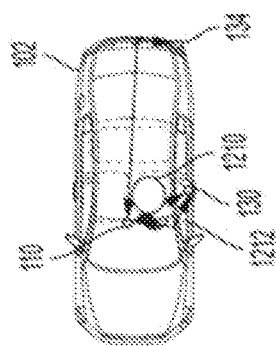
Figure 5A:
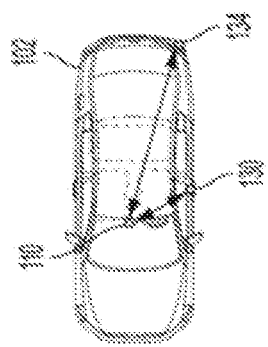

For instance, FIG. 5A illustrates how node 110, 130, and 134 may transmit and receive CIR metadata. Here, system 100 may determine that vehicle 102 is operating in an initial static state where no obstructions exists because the CIR is operating under a LOS condition. In other words, system 100 may determine that the CIR response times received by nodes 110, 130, and 134 indicate there is no obstruction.

In the example illustrated by FIG. 5B, nodes, 110, 130, and 134 are again transmitting and receiving CIR metadata. In this example, however, an obstruction (e.g., a driver) may be situated in the front-driver seat. System 100 may determine based on the reflected CIR 1212 and 1214 that a NLOS operating state exists because a person situated in the front driver seat.

FIG. 5C, again illustrates nodes 110, 130, and 134 transmitting and receiving CIR metadata. In this example, system 100 may again determine a NLOS operating state exists because there is an obstacle 1214 located near vehicle 102.

Figure 6:
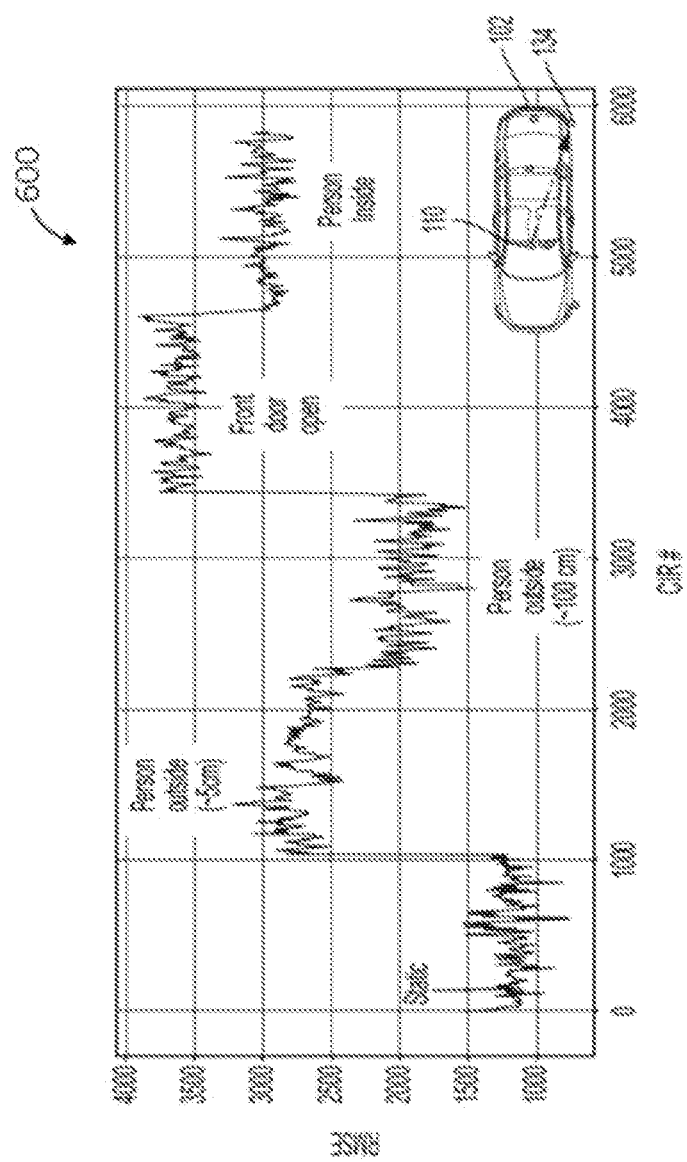
FIG. 6 is an illustrative graph of the root-mean-square energy of received CIR.

FIG. 6 is an exemplary graph 600 illustrating the root-mean-square energy for CIR that may be transmitted by node 110 and received by node 134 during various operating states. FIG. 6 illustrates examples of how the system 100 may process CIR metadata to determine a LOS or N LOS operating state exists. With reference to FIG. 6, CIRs RMSE pattern between 0-1,000 may be used by system 100 to determine the vehicle 102 is operating in a static state with no obstructions. For CIRs RMSE pattern between 1,000-2,000, the system 100 may determine a person may be located approximately 5 centimeters outside the vehicle 102. For CIRs RMSE pattern between 2,500-3,500, the system 100 may determine a person may be located approximately 100 centimeters outside the vehicle 102. For CIRs RMSE pattern between 3,500-4,500, the system 100 may determine a front door of the vehicle 102 is open. And for CIRs RMSE pattern between 4,500-5,500, the system 100 may determine a person is situated within the vehicle 102.

Again, system 100 may also use the results of a machine-learning classification algorithm to determine a given operating state. For instance, system 100 may use the CIR index and amplitude to determine intermediate peaks between a first path, a peak path, and one or more measurable peaks earlier than the first path. System 100 may then use a machine-learning classification algorithm (e.g., random forest), in addition to the decision algorithm applied during step 418, to determine the CIR metadata indicates LOS or NLOS operating state exist due to reflections from far-away obstacles or a heavily attenuated direct path.

It is also contemplated that traditional systems may not be operable to accurately estimate the distance of the target device due to nature of the environment. Traditional systems, for instance, may not be able to accurately provide accurate distance estimations if the vehicle 102 is parked in a garage with walls surrounding the vehicle. System 100 may be operable to provide improved estimated range compensation based on the environment over traditional systems. For instance, a range compensation method may be used where nodes 110-136 may estimate the range in an initial static situation and compare the static range estimate with known values. System 100 may be able to provide such a comparison because nodes 110-136 are static and the range between them will be constant and may be predetermined.

Figure 7:
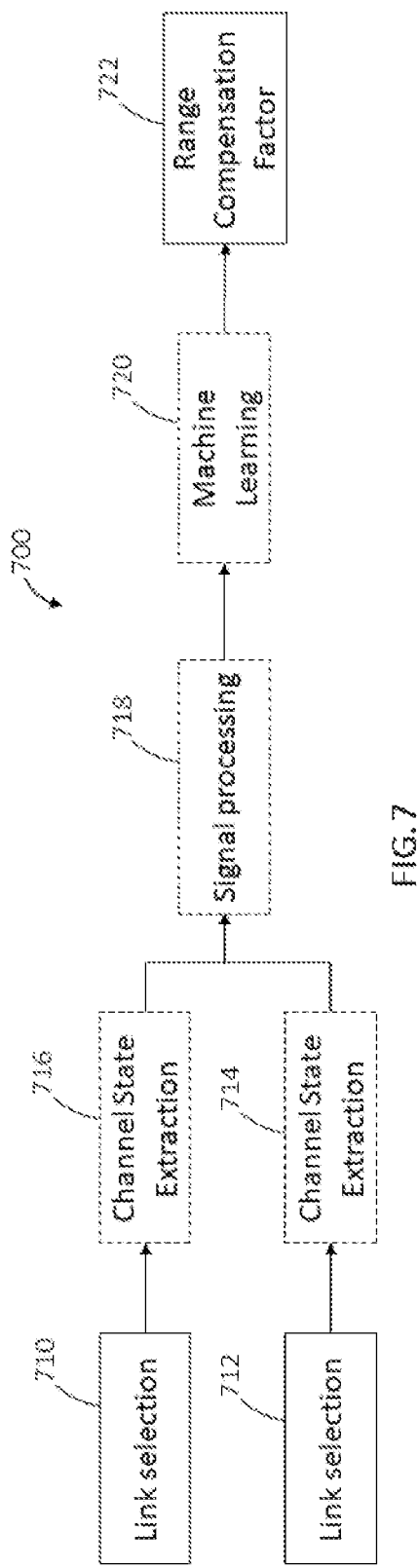
FIG. 7 is an alternate example of an operational diagram of the UWB system.

For instance, FIG. 7 illustrates a low diagram 700 for how system 100 may provide adaptive range compensation. As illustrated by step 710, a link selection may be used during a calibration process to calculate the range between two nodes (e.g., node 110 and 122). The calculated range may be compared with an actual range to determine a base range compensation factor for a given link (e.g., node 110). At step 718, step 720 and step 722, the system 100 may further execute a channel state extraction, signal processing or a machine-learning algorithm like that described with respect to step 412, step 414, and step 416. It is contemplated that during the calibration process, steps 716-720 may be optional and may be employed depending upon the number and location of nodes used by system 100.

Once the calibration process is complete, step 712 may execute a run-time link selection process where for a given link pair (e.g., node 110 and 122) system 100 may calculate a run-time range compensation factor. It is contemplated that at step 714 the system 100 may calculate the range compensation factor using information received or calculated during channel state extraction such as CIR signal strength (i.e., signal strength of the RF signal) or the complete CIR. Step 718 may further employ signal processing that may include cross correlation of the CIR data or a root-mean squared estimation (RMSE) between the CIR data or the CIR metadata. Step 720 may further be used by system 100 to determine the range compensation factor using a machine-learning classification algorithm like the Random Forest classification algorithm. It is again contemplated that during runtime, the range compensation factor may have been pre-determined and steps 716-720 may optional.

It is contemplated that a range compensation factor for a receiver node (e.g., node 110) may be calculated as a median value or mode compensation factor over a subset of transmitter nodes (e.g. nodes 112-136). It is contemplated that the subset of transmitter nodes (e.g. nodes 112-136) may include all possible links for a given receiver node (e.g., node 110). It is also contemplated that only a small subset of transmitter nodes (e.g. nodes 112-136) may include all possible links for a given receiver node (e.g., node 110). For instance, the transmitting node (e.g., node 110) may have a link with just internal receiver nodes (e.g., nodes 112-124) or external receiver nodes (e.g., nodes 126-136). Or the transmitting node (e.g., node 110) may have an active link with the target device 106.

Again, the channel extraction and signal processing employed by steps 714-718 may be optional and the range compensation factor may simply be calculated by system 100 by dividing the default range by a run-time range. When channel state extraction and signal processing are not employed, system 100 may be operable to calculate the range estimation among all links (e.g., nodes 112-136) during run-time. It is contemplated that performing such calculations during run-time may result in increased latency and power consumption for system 100. But, it is also contemplated that such run-time calculations that operate on all links may be desirable as the master transmitting node (e.g., node 110) may be receiving all CIR data and metadata transmitted by the receiving or slave nodes (e.g., nodes 112-136). It is further contemplated that flow diagram 700 may provide improved localization of the target access device.

System 100 may also use the calculated range error to determine an initial compensation factor for each node 110-136. It is contemplated that the compensation factor may be affected by the environment and system 100 may utilize the radio frequency sensing algorithms described above to determine the type of reflection and accordingly derive the compensation factor. It is further contemplated that the compensation factor may also be determined using the CIR RMSE between a given pair of nodes (e.g., between node 110 and node 124).

System 100 may also be operable to activate an intrusion model based on the determined operating state. As explained above, system 100 is operable to determine several operating states (e.g., door open window open, person getting inside). Each of these operating states may be used by system 100 to develop an intrusion model. System 100 may be operable to include an intrusion mode that detects any operating state change or pattern. For instance, system 100 may activate an intrusion mode when the vehicle 102 is parked, the doors and windows are closed, and no person is seated within the vehicle 102. And if a person is located near vehicle 102 (e.g., approximately 1 foot), system 100 may activate the intrusion system (e.g., by activating an audible beep) as a warning. System 100 may activate the audible warning because the person approaching or standing near vehicle 102 is not holding target device 106. System 100 may be further operable to notify an owner of the vehicle that an unidentified person is standing near vehicle 102. System 100 may provide such a warning to the owner's target device 106 (e.g., via text message, mobile phone app, or to a key fob). Such an advanced warning may be desirable in situations where system 100 determines the owner may be approaching the vehicle 102 (e.g., by detecting target device 106 is nearing the vehicle 102).

Figure 8:
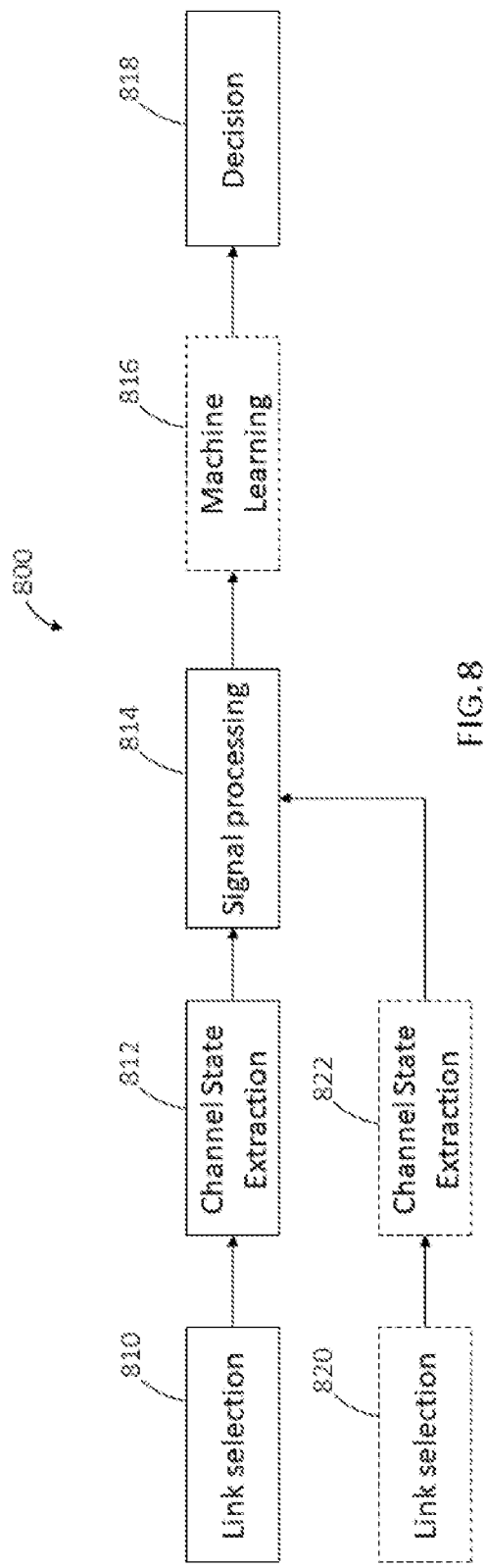
FIG. 8 is an alternate example of an operational diagram of the UWB system.

FIG. 8 illustrates a flow diagram 800 that may be used for the intrusion mode. As shown by steps 810-818, the system 100 may employ a link selection, channel state extraction, signal processing, machine learning, and operating state determination. It is contemplated that steps 810-818 may operate like steps 410-418 described with respect to flow diagram 400. It is also contemplated, however, that system 100 may be operable to provide the intrusion mode using link selection alone.

However, it is further contemplated that system 100 may include additional link selections and channel state extractions. If additional links are added, system 10 may process the channel state information for all additional links together to develop a machine-learning model with respect to a plurality of operating states. Additional links may provide system 100 with the capability of determining a single operating state or a plurality of operating states. For instance, system 100 may be able to determine that the vehicle 102 is locked and that there is a user located within vehicle 102.

System 100 may also be operable to detect (1) user occupancy within vehicle 102; and (2) location of users within vehicle 102. Upon detecting user occupancy within vehicle 102, system 100 may activate additional vehicle systems (e.g., HVAC or infotainment system, front passenger airbag systems) to provide better user experience and safety. For instance, system 100 may detect when a rear seat is occupied and provide an audible warning if the user has not engaged a seatbelt when the vehicle 102 is in motion. Additionally, system 100 may engage certain climate control settings based on the number of users situated within the vehicle 102. It is contemplated that occupancy and location detection may be accomplished using flow diagram 800. Occupancy and location detection may therefore be accomplished using a single link selection. Or occupancy and location detection may use additional link selection and channel state extraction so that system 100 may detect a plurality of different operating states.

System 100 may also be operable to detect human activity within the vehicle 102. For instance, nodes 110-124 (i.e., inside nodes) may be used to detect sudden human commotion or activity within the vehicle 102, system 100 may be able to make such a detection because sudden movements may have a larger effect on the CIRs received by nodes 110-124. For instance, a user may be choking on food and making extreme and sudden arm movements. If system 100 determines no other users are within the vehicle 102, system 100 may detect the sudden movements and infer that emergency services should be contacted. Such human activity detection may also be advantageous for use in autonomous vehicles where users may not be actively paying attention to the vehicle operation or surroundings.

It is contemplated that human activity detection may be accomplished using flow diagram 800. Occupancy and location detection may therefore be accomplished using a single link selection. Or human activity detection may also use additional link selection and channel state extraction so that system 100 may detect a plurality of different operating states.

System 100 may also be operable to monitor vital signs of users within the vehicle 102. For instance, system 100 may be able to determine breathing and heart rate of the passengers because nodes 110-136 may operate at a higher timing resolution (e.g., 200 picoseconds). System 100 may be operable to further use the vital sign information for detecting human emotions. Using any number of vital sign parameters, system 100 may be able to detect medical emergency situations, safety use cases (e.g. determining human bursts/violent reaction while it is building up), or enhanced user experience settings (e.g., control music/temperature/dashboard lights). System 100 may further use the monitored vital sign information to differentiate between a user and an inanimate object (e.g., grocery bags or a box). It is also contemplated that nodes 110-136 may operate at an even higher timing resolution (e.g., 100 picoseconds) such that system 100 may be able to differentiate between an adult and child present within the vehicle. System 100 may be operable to make this distinction due to the differences between the breathing rate, heart rate, and movement between adults and children.

Figure 9:
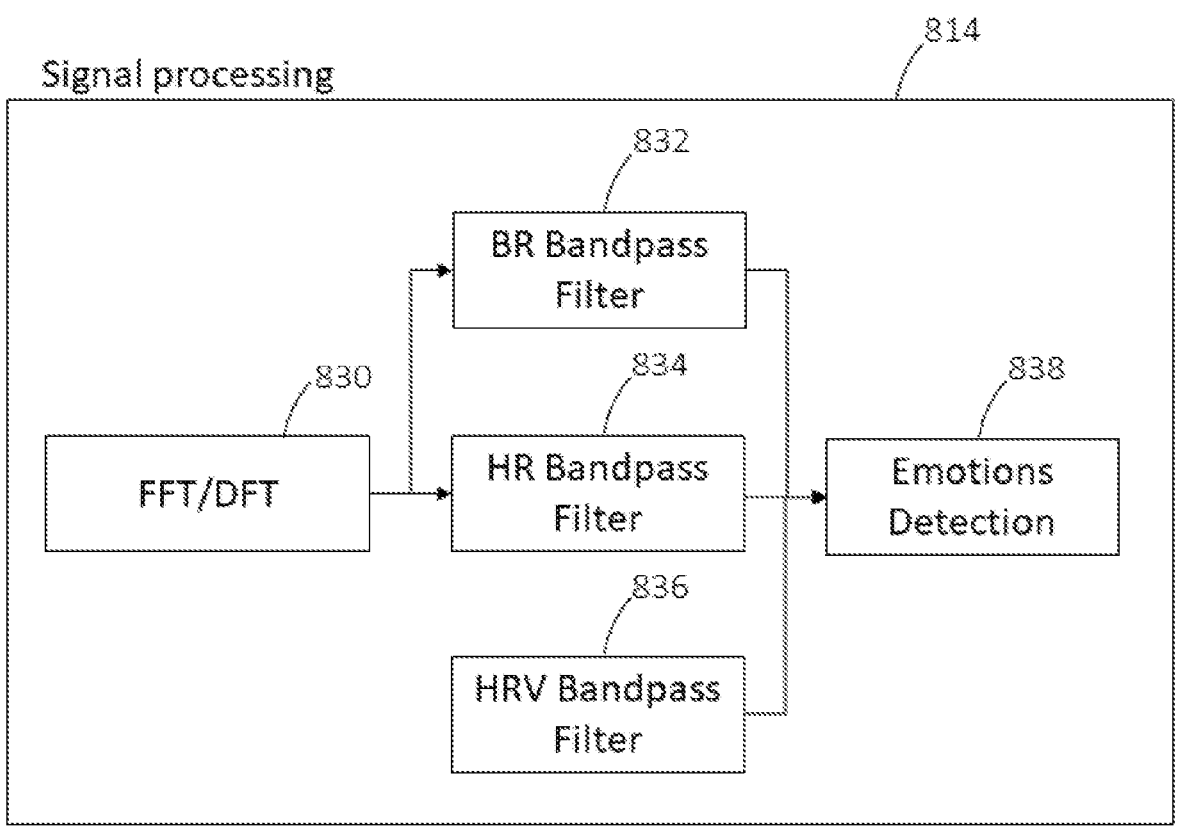
FIG. 9 is an illustrative example of signal processing algorithms that may be employed by UWB system; and, FIG. 10 is an alternate example of an operational diagram of the UWB system.

It is contemplated that flow diagram 800 may also be used for detecting vital signs monitoring. System 100 may again include a single link selection or more than one link selections to provide data that may be used to determine a user's vital signs. Signal processing may be programmed with various algorithms for determining breathing rate and heart rate based on the CIR data received. For instance, FIG. 9 illustrates various algorithms that may be employed by signal processing. As shown, signal processing may process CIR data using a Fast Fourier Transform (FFT) and/or Discrete Wavelet Transform (DWT) algorithm. Step 814 may further be operable to include a breathing rate bandpass filter, heart rate band pass filter, and a heart rate variability (HRV) bandpass filter. An emotion detection algorithm may receive and further process the data received by steps 830-834.

System 100 may further be operable to differentiate between different users of vehicle 102. For instance, a first user may approach vehicle 102 while holding target device 106. Using the reflection introduced by the first user walking toward the vehicle 102, system 100 may be able to identify the first user from other stored profiles associated with other users. System 100 may be able to perform such user identification by storing and analyzing certain parameters that may include a user's unique walking style or the physical dimensions of the user. The unique reflection patterns received by nodes 110-136 may be compared by system 100 to a stored user profile to make such an identification.

It is contemplated that user differentiation may be accomplished using flow diagram 800. Occupancy and location detection may therefore be accomplished using a single link selection. Or user differentiation may also use additional link selection and channel state extraction so that system 100 may detect a plurality of different operating states. It is also contemplated that several registered users may be preprogrammed and used by step 818 for detecting different users.

System 100 may further be operable to provide increased awareness of the environment surrounding the vehicle 102. Again, system 100 may be operable to determine if the vehicle 102 is situated in a parking lot or if the vehicle 102 is parked next to another vehicle (e.g., FIG. 5C). System 100 may be operable to process the information received to enhance accuracy of access control system by adjusting range estimates as a function of a surrounding multipath profile.

It is contemplated that environmental awareness may be accomplished using flow diagram 800. Environmental awareness may therefore be accomplished using a single link selection. Or environmental awareness may also use additional link selection and channel state extraction so that system 100 may detect a plurality of different operating states. It is also contemplated that environmental awareness may likely rely more on external nodes (i.e., nodes 126-136) and less on internal nodes (i.e., nodes 110-124).

As mentioned above, system 100 may also provide enhanced security against relay attacks. System 100 may provide such increased security because a received CIR pattern by nodes 110-136 may be matched with CIR pattern received by target device 106. System 100 may be operable to determine a high cross correlation between the received CIR pattern to establish authenticity of the communication pair.

Figure 10:
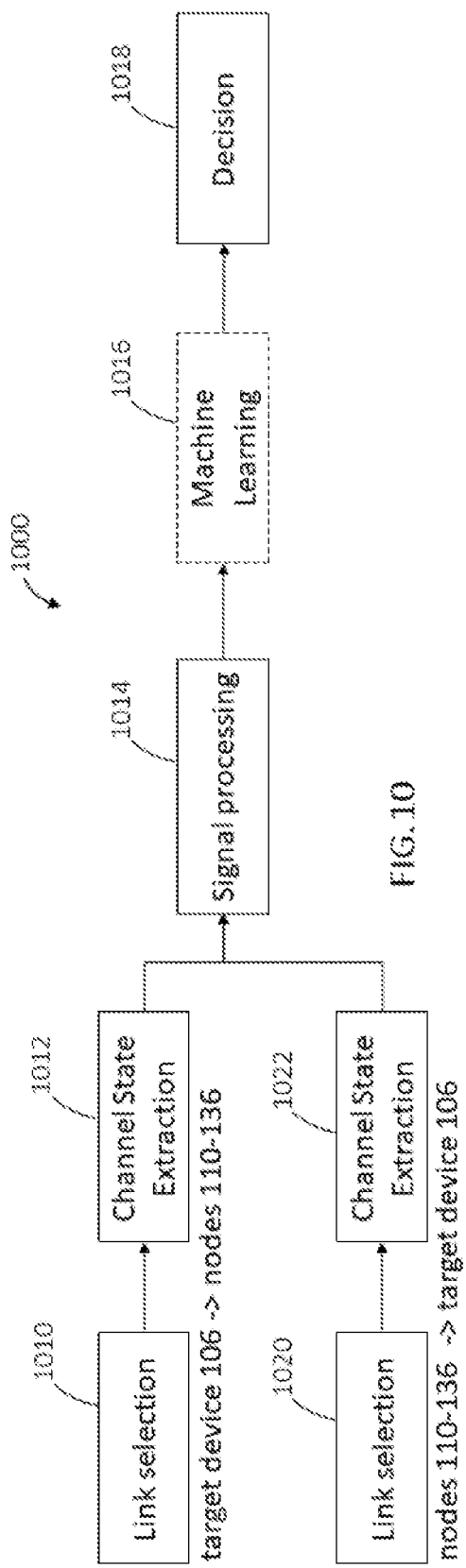

FIG. 10 illustrates a flow diagram 1000 that may be used for enhanced security against relay attacks. At step 1010, a first link selection may communicate CIR data from a target device 106 to one of nodes 110-136. At step 1020, a second link may be communicate CIR data from one of nodes 110-136 to target device 106. It is contemplated that the channel state information between one of the nodes 110-136 and target device 106 may be matched to ensure there is not another device located in-between the nodes 110-136 and the target device 106. For instance, node 110 may send message to the target device 106; and the target device 106 may reply with corresponding message to node 10 along with CIR data of message received from node 110. Node 110 may then correlate the data received with CIR data obtained from the target device 106. It is contemplated that the message exchange between node 110 and target device 106 may occur within 1 millisecond. It is also contemplated that the channel may be stationary thereby resulting in a high correlation between the two CIRs when there is no additional device in between node 110 and target device 106. System 100 may detect when another device is in-between because the CIR detected by target device 106 and node 110 may be different resulting in a lower correlation. It is also contemplated that the channel state extraction, signal processing, machine-learning algorithm and operating state decision executed at steps 1012-1018 and step 1022 may operate like steps 412-418 described above.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data, logic, and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

The following applications are related to the present application: U.S. patent application Ser. No. 16/368,994, filed on Mar. 29, 2019. The identified application is incorporated by reference herein in its entirety.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of determining an operating state, the method comprising:
   selecting one or more transmitting nodes within a first transceiver unit having a first processor for transmitting one or more radio-frequency (RF) signals;
   receiving the one or more RF signals at one or more receiving nodes within a second transceiver unit having a second processor,
   wherein the one or more RF signals include one or more channel state data;
   determining the operating state based on one or more features extracted from the one or more channel state data within the second processor; and
   wherein the one or more transmitting nodes located within a vehicle transmits an ultra-wide band (UWB) signal;
   wherein the one or more receiving nodes includes a target device located outside the vehicle to receive the UWB signal;
   transmitting from the target device a response message to the one or more transmitting nodes, wherein the response message includes a first channel impulse response (CIR) data that is calculated from the UWB signal; and
   determining an authenticity between the one or more transmitting nodes and the one or more receiving nodes based on a correlation between the first CIR data included within the response message and a second CIR data computed from the response message.

2. The method of claim 1, wherein the one or more channel state data include channel impulse response (CIR).

3. The method of claim 1, wherein the one or more channel state data include signal strength of the RF signal.

4. The method of claim 1, wherein the one or more channel state data include at least one of a peak position, amplitude, or phase.

5. The method of claim 1 further comprises:
   processing the one or more channel state data using a Fast Fourier Transformation (FFT) algorithm and a Discrete Wavelet Transform (DFT) algorithm;
   filtering the one or more channel state data using one or more bandpass filtering algorithms; and
   detecting a user heart rate, a user breathing rate, or a user emotional state.

6. The method of claim 1, wherein the determining the operating state further comprises: estimating a number of living beings within a vehicle.

7. The method of claim 1, wherein the determining the operating state further comprises: differentiating between an inanimate object and a human.

8. The method of claim 1, wherein the determining the operating state further comprises: differentiating between an adult and a child.

9. The method of claim 1, wherein the one or more channel state data may include one or more channel impulse responses (CIR); and determining sudden user activity within a vehicle by detecting changes in the one or more channel impulse responses.

10. The method of claim 1, wherein determining the operating state further comprises: differentiating between a first user and a second user based on reflection patterns detected within the one or more channel state data.

11. The method of claim 1, wherein the determining the operating state further comprises: detecting an intrusion in a vehicle.

12. The method of claim 1 further comprises:
   determining the operating state by processing the one or more channel state data using a machine-learning classification algorithm.

13. The method of claim 1, wherein the one or more transmitting nodes includes a target device located outside a vehicle that transmits an ultra-wide band (UWB) signal; wherein the one or more receiving nodes located within the vehicle receive the UWB signal; transmitting from the one or more receiving node a response message to the target device, wherein the response message includes a first CIR data that is calculated from the UWB signal; and determining an authenticity between the one or more transmitting nodes and the one or more receiving nodes based on a correlation between the first CIR data included within the response message and a second CIR data computed from the response message.

14. A method of determining a range compensation value, the method comprising:
   transmitting a radio-frequency (RF) signal from at least one transmitting node;
   receiving the RF signal at one or more receiving nodes;
   estimating a channel state data from the RF signal;
   receiving a position value indicating a location of the at least one transmitting node;
   determining the range compensation value using the channel state data and the position value; and
   wherein the one or more transmitting nodes located within a vehicle transmits an ultra-wide band (UWB) signal;
   wherein the one or more receiving nodes includes a target device located outside the vehicle to receive the UWB signal;
   transmitting from the target device a response message to the one or more transmitting nodes, wherein the response message includes a first channel impulse response (CIR) data that is calculated from the UWB signal, and determining an authenticity between the one or more transmitting nodes and the one or more receiving nodes based on a correlation between the first CIR data included within the response message and a second CIR data computed from the response message.

15. The method of claim 14, wherein the channel state data includes a CIR of the RF signal.

16. The method of claim 14, calculating a statistical range correction factor for at least one of the receiving nodes; and adjusting an estimated range using the statistical range correction factor.

17. The method of claim 14, wherein the range compensation value is estimated using sensed environmental conditions.

18. The method of claim 14, wherein the range compensation value is adjusted based on a correlation of the channel state data with training data obtained during a machine-learning training process.

19. A system operable to determine an operating state, the system comprising:
   one or more transmitting nodes operable to transmit one or more radio-frequency (RF) signals;
   one or more receiving nodes operable to receive the one or more RF signals, wherein the one or more RF signals include one or more channel state data; and
   a controller in communication with the one or more transmitting nodes and receiving nodes, wherein the controller is operable to:
   receive the one or more RF signals;
   determine the operating state based on one or more features extracted from the one or more channel state data; and wherein the one or more transmitting nodes located within a vehicle transmits an ultra-wide band (UWB) signal, wherein the one or more receiving nodes includes a target device located outside the vehicle to receive the UWB signal;

transmitting from the target device a response message to the one or more transmitting nodes, wherein the response message includes a first channel impulse response (CIR) data that is calculated from the UWB signal; and determining an authenticity between the one or more transmitting nodes and the one or more receiving nodes based on a correlation between the first CIR data included within the response message and a second CIR data computed from the response message.

* * * * *